(12) United States Patent
Milosevic

(10) Patent No.: US 7,961,310 B1
(45) Date of Patent: Jun. 14, 2011

(54) TRANSMISSION LIQUID FLOW CELL WITH INCREASED INTERNAL FLOW RATES

(75) Inventor: Milan Milosevic, Westport, CT (US)

(73) Assignee: Durasens, LLC, Pleasantville, NY (US)

( * ) Notice: Subject to any disclaimer, the term of this patent is extended or adjusted under 35 U.S.C. 154(b) by 103 days.

(21) Appl. No.: 12/459,887

(22) Filed: Jul. 9, 2009

Related U.S. Application Data

(60) Provisional application No. 61/134,436, filed on Jul. 9, 2008.

(51) Int. Cl.
*G01N 1/10* (2006.01)

(52) U.S. Cl. .................................. 356/246; 356/440

(58) Field of Classification Search ............ 356/244, 356/246, 436, 440, 73; 422/82.05, 82.09; 250/428–438, 373, 576; 435/288.5; 73/36, 73/61, 69, 64, 43, 30
See application file for complete search history.

(56) References Cited

U.S. PATENT DOCUMENTS

| | | | | |
|---|---|---|---|---|
| 3,740,156 A * | 6/1973 | Heigl et al. | ............ | 356/433 |
| 3,810,695 A * | 5/1974 | Shea | ............ | 356/73 |
| 4,872,753 A * | 10/1989 | Danigel et al. | ............ | 356/246 |
| 5,003,174 A * | 3/1991 | Datwyler et al. | ............ | 250/343 |
| 5,046,854 A * | 9/1991 | Weller et al. | ............ | 356/440 |
| 5,223,716 A * | 6/1993 | Rossiter | ............ | 250/343 |
| 5,241,368 A * | 8/1993 | Ponstingl et al. | ............ | 356/436 |
| 5,371,020 A * | 12/1994 | Frischauf | ............ | 436/165 |
| 5,404,217 A * | 4/1995 | Janik et al. | ............ | 356/246 |
| 5,521,384 A * | 5/1996 | Lynch | ............ | 250/343 |
| 6,587,195 B1 * | 7/2003 | Jennings | ............ | 356/246 |

* cited by examiner

*Primary Examiner* — Tarifur R Chowdury
*Assistant Examiner* — Michael LaPage

(57) ABSTRACT

The present invention relates to a transmission liquid flow cell capable of high rates of liquid flows regardless of the optical pathlength of the cell. This increase in the cell's internal flow rate is provided by an internal bypass created around the circumference of the windows. The high rate of internal flow of liquid around the circumference of the windows and in direct contact with the liquid between the windows provides a push-pull action that urges the flow of liquid through the gap between the windows. The faster the circumferential flow, the stronger the push-pull action. The cell is used for the measurement of the absorption of light passing through a liquid sample contained in the gap between the cell's windows.

3 Claims, 3 Drawing Sheets

TRANSMISSION LIQUID FLOW CELL WITH INCREASED INTERNAL FLOW RATES

CROSS-REFERENCE TO RELATED APPLICATIONS

Figure 1:
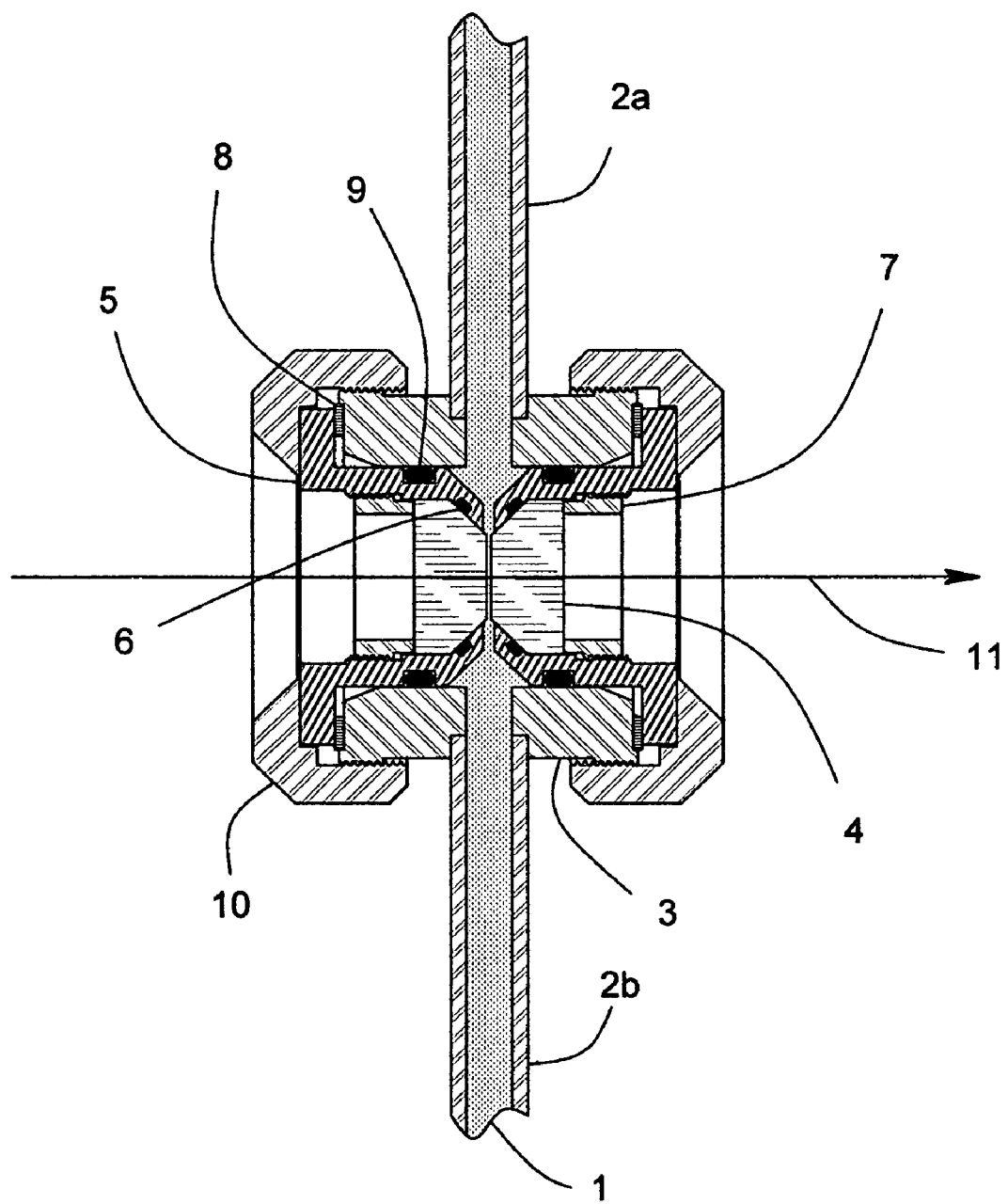

This application claims the benefit of provisional patent application Ser. No. 61/134,436, filed 2008 Jul. 9 by the present inventor.

FEDERALLY SPONSORED RESEARCH

Not Applicable

SEQUENCE LISTING OR PROGRAM

Not Applicable

BACKGROUND

1. Field of Invention

This invention relates to the analysis of liquid samples by transmission spectroscopy, specifically to a flow cell with an improved flow of sample.

2. Prior Art

Optical transmission liquid cells are well known and widely utilized in measuring the optical properties of liquid samples. The general configuration of these cells includes two substantially parallel optical windows spaced a certain distance apart thus forming a gap between them into which a liquid sample can be introduced. A cell body holds windows in place in a leak proof way and usually incorporates an inlet and an outlet for the sample.

The windows of the cell are made of a material that is transparent to light in the spectral region of interest. For visible light the most commonly used window material is glass. Quartz is the material of choice for the ultraviolet spectral region. A large selection of materials, such as NaCl, KBr, CaF2, etc., are used in the infrared region. The window material is selected for optical transparency, chemical compatibility with the sample of interest, mechanical strength, temperature range, refractive index, etc. The gap between the two windows establishes the pathlength of light through the sample. As light passes through the sample, different wavelengths of light are absorbed differently by the sample. This selective absorption of light by a sample is a unique characteristic of the sample and can be used to identify unknown samples, quantify the concentration of a sample in a mixture, elucidate molecular structure of unknown samples, etc. The cell can be used in a static configuration where the cell is filled for analysis, for instance with a syringe, and the sample is stationary during the analysis, or in a flow through configuration where the sample is flown through the cell for analysis.

The optical pathlength is the most important parameter of a transmission cell. The pathlength determines the strength of absorption of light by the sample in the cell. The longer the pathlength through the sample the stronger the absorption of light by the sample. It is generally known that the optimum cell pathlength for a particular sample is one that provides for an absorption of about 63% of the incident light. In the visible and near infrared spectral regions most liquids absorbs light weakly and transmission cells in that spectral region employ longer pathlengths through the sample, 10 mm being the most common pathlength used. Such pathlengths do not present a substantial resistance to the flow of liquid through the cell. Thus transmission flow cells having longer pathlengths (generally more than 1 mm) are very common.

However, the mid-infrared spectral region, also known as the fingerprint region, which is characterized with strong sharp spectral absorption peaks highly characteristic of the sample requires submillimeter pathlengths, thus high flow rates through such cells are not possible. For instance, a 100 μm pathlength is typical for transmission cells that operate in the infrared spectral region. Clearly, very short pathlengths impede the flow of liquid between the two windows and particularly so for viscous samples. However, even for less viscous samples the narrow space between the windows becomes a great impediment to the flow of sample through the cell. In addition to slowing the flow of liquid through the cell, a short pathlength also makes such a cell vulnerable to clogging by particulates in the liquid. This greatly reduces the usefulness of transmission cells with submillimeter pathlengths for routine fluid monitoring applications where a flow-through operation is essential.

To monitor liquids using a transmission cell, usually a slip stream is set up to flow the liquid through the cell for analysis. Thus the liquid must travel through the slip steam from the intake point to the cell. To perform a spectroscopic analysis of the liquid present in the cell, light is passed through the cell and the absorption of light by the sample in the cell is measured. The result of the analysis reflects the state of the liquid at the intake point as it was at the time it was extracted into the slip stream. If the flow of sample through the cell is slow, the information obtained by the analysis significantly lags behind the status of the liquid at the point of extraction. While preferable to grabbing a sample and analyzing it offline, in most situations this delay is still undesirable, and potentially very costly, thereby limiting the utility of the analysis. Thus, if possible, it would be extremely useful, for those cases where the required pathlength of the transmission cell has to be in the submillimeter range, to have the cell constructed in such a way to enable a high flow of sample through the cell. One way to improve the flow through the bypass loop, known in the art, is to add a secondary bypass into the main bypass line very close to the cell that shunts most of the liquid flow around the cell leaving only a small fraction of the flow to travel through the cell. This secondary bypass with slow flow, as dictated by the cell, can be made close to the cell thus shortening the path along which the flow of liquid is very slow. The overall liquid flow through the bypass loop consists of the fast flow through most of the bypass loop and a short section of slow flow through the secondary bypass. This helps reduce the delay caused by the transit time of liquid from the intake point to the cell.

SUMMARY

The present invention is a transmission flow liquid cell, used for the measurement of the absorption of light passing through a liquid sample, which is capable of high rates of flow of sample through the cell regardless of the optical pathlength of the cell. In many cases the optical pathlength of the cell must be very short, a fraction of a millimeter, which considerably limits the rate of flow of liquid through the cell. By increasing the flow rate through the cell, the present invention extends the usability of transmission flow cells to the cases where a short pathlength is required for analysis. This increase in the cell's internal flow rate is provided by an internal channel around the circumference of the internal cavity of the cell, along which liquid flows at a high rate. This high rate of internal flow is two foldly beneficial. First, it provides a path of high flow through the cell so the cell can be used on a fast flowing slip stream. Second, the fast flow of liquid around the gap and in direct contact with the gap provides a push-pull action that urges the flow of liquid through the narrow gap between windows. The faster the circumferential flow, the stronger the push pull action.

DRAWINGS

Figures

FIG. 1 shows a cross-sectional view of one possible embodiment of the present invention. The main axis of the cell also indicates the path of the optical beam which passes perpendicular to the windows and through sample contained in the gap between the windows.

Figure 2:
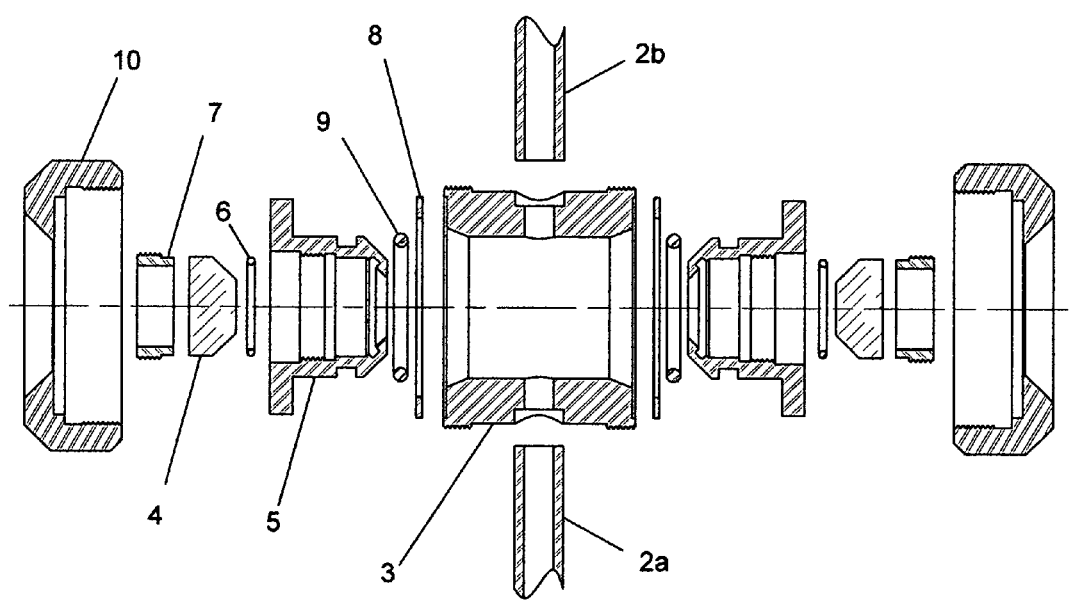

FIG. 2 shows the 'exploded' view of the cell that is shown assembled in FIG. 1. The same numerals are used to identify equivalent parts in FIGS. 1 and 2. O-rings are also shown outside their o-ring grooves and the inlet and outlet tubes are shown unattached to the cell body.

Figure 3:
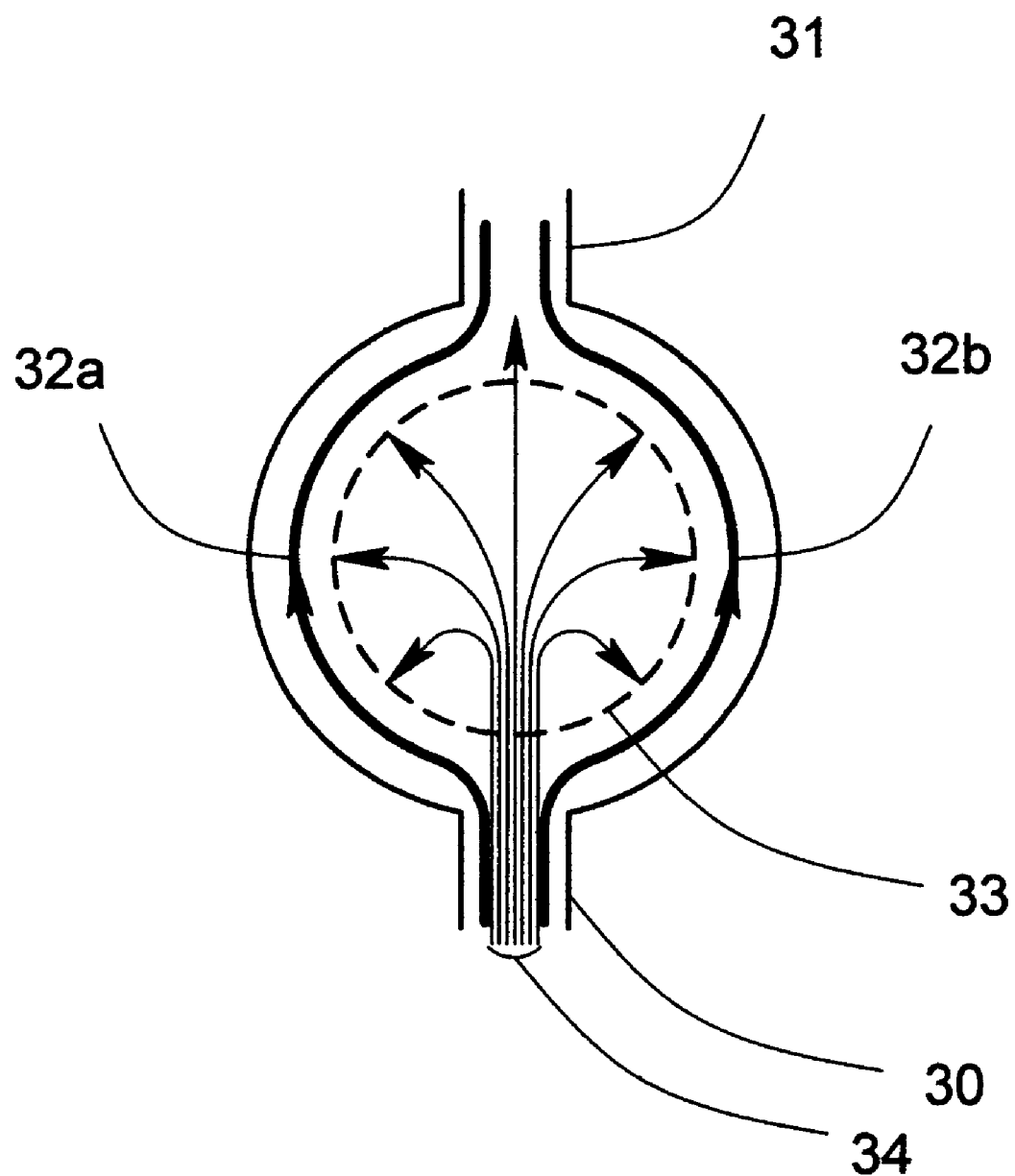

FIG. 3 shows the conceptual flow pattern for the cell of present invention viewed perpendicular to optical beam. Flow lines that enter the gap between two windows are indicated with thin curved lines with arrows showing flow direction. Thick heavy lines indicate the bypass circumferential flow.

REFERENCE NUMERALS

1. Liquid sample
2a. Outlet tube
2b. Inlet tube
3. Cell body
4. Window (2)
5. Insert (2)
6. Window o-ring (2)
7. Compression ring (2)
8. Spacer (2)
9. Insert o-ring (2)
10. Compression nut (2)
11. Cell axis
30. Incoming flow
31. Outgoing flow
32a. Left bypass flow
32b. Right bypass flow
33. Dashed line indicating the gap area between windows
34. Flow lines

DETAILED DESCRIPTION OF THE PREFERRED EMBODIMENTS

One embodiment of the cell for the analysis of a flowing liquid sample 1 is shown assembled in FIG. 1 and disassembled in FIG. 2. The input tube 2b and output tube 2a are positioned substantially in the center of the cell and opposite each other. The cell is left right symmetric, i.e. the left side of the cell is the mirror image of the right side. For each component shown on the left side there is an identical component shown on the right side and vice versa. For clarity, we have identified only one component of each pair.

Input tube 2b and output tube 2a are in a leak proof fashion (welded, glued, o-ring sealed, etc.) attached to the cell body 3 centered on the respective holes in the body. Each end of the body is enclosed with opposing inserts 5 sealed to the body's inner wall by o-rings 9. Optical windows 4 are sealed into the inserts by o-rings 6 and held in place by retaining rings 7. The windows could also be glued or brazed into the inserts in which case said o-rings 6 and said retaining rings 7 would not be used. At the inner ends said inserts 5 taper towards the axis 11 with both the outside and inside surface. The optical windows are beveled to match the inside taper of the inserts. The wring grooves for o-rings 6 are cut into the inside tapers of the inserts so that, by tightening the retaining rings 7, said windows 4 can compress said o-rings 6 into said o-ring grooves by their tapered sides to form face seals. When inserted into the cell body, said inserts 5 enclose a sealed path from the inlet 2b through the gap between the two windows to the outlet 2a. Inserts 5 are pushed into the cell until they are stopped by spacers 8. In this way a known gap is formed between said two windows 4. The size of said gap can be controlled by changing the thickness of said spacers 8. The flat face of each window on the beveled side protrudes slightly out of the insert so that said gap can be arbitrarily small. Retaining nuts 10 hold said inserts 5 secured in place.

The outside tapers of the inserts form a ring shaped bypass that follows the circumference of the windows and that provides for an inside fast flow of liquid regardless of the pathlength. Another way to provide this circumferential bypass is to cut a groove into the inside bore of the body so that the inlet and outlet openings in the body are centered on said groove.

FIG. 3 shows conceptually how the liquid flows through the cell. The liquid enters the cell from the inlet 30. The strong flow of liquid coming through the inlet pushes the liquid into the gap, but most of the flow is deflected around the circumference of the cell windows to the outlet 31, where it exits the cell. The circumferential flow splits at the inlet 30 into two streams, the left bypass flow 32a and the right bypass flow 32b, each traveling along a separate semicircular path around the windows until they reunite at the outlet 31.

The fast circumferential flow 32a and 32b is outside and around the gap 33 formed by the two windows, where light passes through the cell and thus it does not interfere with optical measurements. The fast forward flow at the inlet 30 provides positive pressure for liquid to enter the gap between the windows. In addition, the fast flow of liquid around the circumference of the gap provides a siphoning action which, according to Bernoulli's principle, pulls the liquid out of the gap area into the fast flowing stream, similarly as fast flowing water creates a vacuum in a laboratory aspirator.

Thin flow lines 34, with arrows indicating the flow directions, show conceptually the flow configuration of liquid inside the gap. This positive push and pull action of the liquid flowing fast around the periphery is possible since the two flows are in direct contact all around the edge of the gap. Therefore the liquid inside the gap is, by this dual action, urged to flow through the gap, and the faster the circumferential flow the stronger the push-pull action.

Note that this is much more preferable to simply increasing the pressure on the inlet side of the cell and letting the increased pressure force a higher flow through the cell. The pressure drop would be highest along the straight line through the gap between the inlet and the outlet, which could force a high flow zone along that straight line while leaving stagnant areas outside this zone. Liquid present in those stagnant zones is still in the area interrogated by the optical beam thus mixing the new information obtained from the measurement from the new fast moving liquid and the older stagnant liquid.

In the cell of the present invention, the push-pull action urges liquid to flow through the entire area of the gap without any stagnant zones as indicated by the flow lines 34. Note that the push-pull action is absent in the prior art case with a secondary bypass loop. The cell is readily disassembled for maintenance or repair.

While the above specification contains many specificities, these should not be construed as limitations on the scope of invention, but rather as an exemplification of a preferred embodiment thereof. Many other variations are possible. For example, the cell may have a rectangular rather then a round body, the inlet and outlet tubing may not be permanently attached, but can for instance have NPT threaded ports to which the input and output tubes, terminated with threaded plugs, are connected. Also, the inserts do not have to be beveled, but could be for instance stepped instead, etc. as long as a circumferential bypass channel is formed for the liquid to flow through.

Accordingly, the scope of the invention should be determined not by the embodiment illustrated, but by the appended claims and their legal equivalents.

I claim:

1. A transmission cell for the measurement of the absorption of light by a liquid comprising; a cell body with inlet and outlet tubes attached to said cell body and creating a pathway to an inner bore of said cell which is sealed on both ends by inserts, each of said inserts having an insert inner bore with a tapered surface on the side towards the center of the cell which is sealed by an optical window on one side of each insert inner bore, an o-ring groove cut into said insert inner tapered surfaces and where said optical windows are discs with one side beveled to match an angle of said insert inner tapered surface so that an o-ring can be compressed by said beveled face of said optical windows said o-ring groove to achieve a face seal between said optical windows and said insert and a flat face of said optical windows protrudes through the tapered end of said insert, said inserts being oriented window to window and forming a gap in the middle portion of said cell body so that, when said cell is filled with liquid, said gap establishes path length through said liquid for light passing through said gap, and where said gap is enlarged near the circumference of said inserts providing a channel for the liquid to flow around a narrow gap between said optical windows thereby allowing an unimpeded flow of liquid through said cell regardless of the size of said gap.

2. The cell from claim 1 where said inserts having an outside surface beveled on the side nearer the center of said cell, said bevels thus forming a circumferential path of a triangular cross section through which liquid can flow around said tapered ends of said inserts thus making said flow through said cell substantially independent of the size of said gap between said windows.

3. The cell from claim 1 where said body of the cell has a groove cut into the wall of the inner bore at the center of said cell providing a circumferential path around said inner bore making said flow through said cell substantially independent of the size of said gap between said windows.

\* \* \* \* \*